United States Patent
DeWit et al.

(10) Patent No.: US 9,040,131 B2
(45) Date of Patent: *May 26, 2015

(54) DIAMOND WINDOW COMPONENT FOR A LASER TOOL

(75) Inventors: Hendrikus Gerardus Maria DeWit, Cuijk (NL); Gerrit Jan Pels, Cuijk (NL)

(73) Assignee: Element Six N.V. (NL)

(*) Notice: Subject to any disclaimer, the term of this patent is extended or adjusted under 35 U.S.C. 154(b) by 129 days.

This patent is subject to a terminal disclaimer.

(21) Appl. No.: 13/811,261

(22) PCT Filed: Jul. 26, 2011

(86) PCT No.: PCT/EP2011/062848
§ 371 (c)(1),
(2), (4) Date: May 22, 2013

(87) PCT Pub. No.: WO2012/013687
PCT Pub. Date: Feb. 2, 2012

(65) Prior Publication Data
US 2013/0236735 A1    Sep. 12, 2013

Related U.S. Application Data

(60) Provisional application No. 61/369,172, filed on Jul. 30, 2010.

(30) Foreign Application Priority Data

Jul. 30, 2010    (GB) .................................. 1012764.5

(51) Int. Cl.
*B32B 1/00*    (2006.01)
*A61N 5/06*    (2006.01)
(Continued)

(52) U.S. Cl.
CPC ........... *A61B 18/201* (2013.01); *Y10T 428/131* (2015.01); *Y10T 428/13* (2015.01);
(Continued)

(58) Field of Classification Search
CPC . A61B 18/201; Y10T 428/13; Y10T 428/131
USPC .................... 428/34.1, 34.4–34.7, 35.7–35.9, 428/36.4–36.6, 36.8–36.9; 604/20, 22; 606/11, 15, 16; 607/89, 100, 154
See application file for complete search history.

(56) References Cited

U.S. PATENT DOCUMENTS 3,895,313 A    7/1975    Seitz
4,170,997 A    10/1979    Pinnow et al.
(Continued)

FOREIGN PATENT DOCUMENTS

EP    1921477 A2    5/2008
GB    1557546 A1    12/1979
(Continued)

OTHER PUBLICATIONS

International Search Report for PCT/EP2011/062848 dated Oct. 19, 2011.
(Continued)

*Primary Examiner* — Walter B Aughenbaugh
(74) *Attorney, Agent, or Firm* — Byran Cave LLP

(57) ABSTRACT

A component for a laser tool, the component comprising: a tubular body defining an internal channel and an aperture; and a window disposed across the aperture and bonded to the tubular body around the aperture, wherein the window is diamond, and wherein the tubular body comprises a material having a coefficient of linear thermal expansion α of $14 \times 10^{-6}$ $K^{-1}$ or less at 20° C. and a thermal conductivity of 60 $Wm^{-1}K^{-1}$ or more at 20° C.

25 Claims, 1 Drawing Sheet

(51) Int. Cl.
*A61B 18/20* (2006.01)
*G02B 23/24* (2006.01)
*A61B 18/22* (2006.01)
*A61B 18/24* (2006.01)
*A61B 18/00* (2006.01)

(52) U.S. Cl.
CPC .......... *Y10T428/12361* (2015.01); *A61B 18/22* (2013.01); *A61B 18/24* (2013.01); *A61B 2018/00095* (2013.01); *A61B 2018/2255* (2013.01); *G02B 23/2492* (2013.01)

(56) References Cited

U.S. PATENT DOCUMENTS

| | | | |
|---|---|---|---|
| 5,322,507 A | 6/1994 | Costello et al. | |
| 6,104,853 A | 8/2000 | Miyagi et al. | |
| 8,842,950 B2 * | 9/2014 | Dewit et al. | 385/43 |
| 2006/0113546 A1 | 6/2006 | Sung | |
| 2009/0287197 A1 | 11/2009 | Hanley et al. | |
| 2009/0287199 A1 | 11/2009 | Hanley et al. | |

FOREIGN PATENT DOCUMENTS

| | | | | |
|---|---|---|---|---|
| GB | 2423816 | * | 9/2005 | ............ G01N 21/55 |
| JP | 63247710 A | | 10/1988 | |
| JP | 05-095962 | | 4/1993 | |
| JP | 09-028715 | | 2/1997 | |
| JP | 2007-202746 A | | 8/2007 | |
| JP | 2007-217753 A | | 8/2007 | |
| WO | 82/02604 A1 | | 8/1982 | |
| WO | 99/00062 A1 | | 1/1999 | |
| WO | 01/49194 A2 | | 7/2001 | |

OTHER PUBLICATIONS

Search Report for GB 1112846.9 dated Aug. 23, 2011.

* cited by examiner

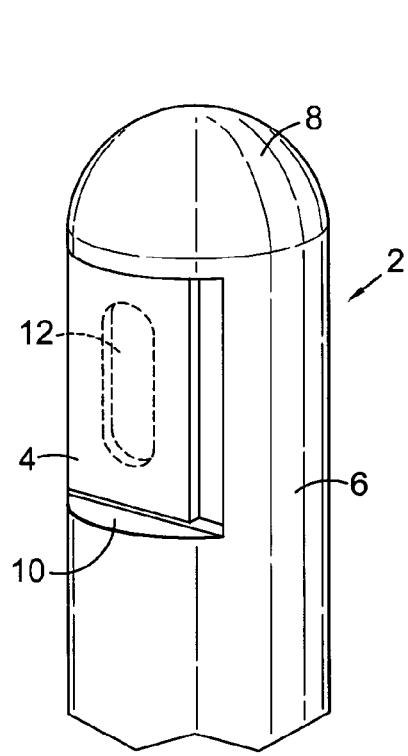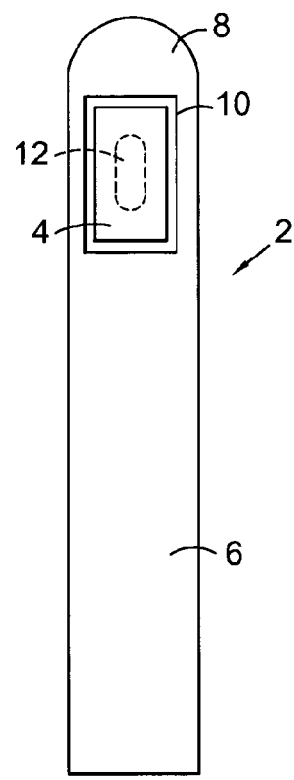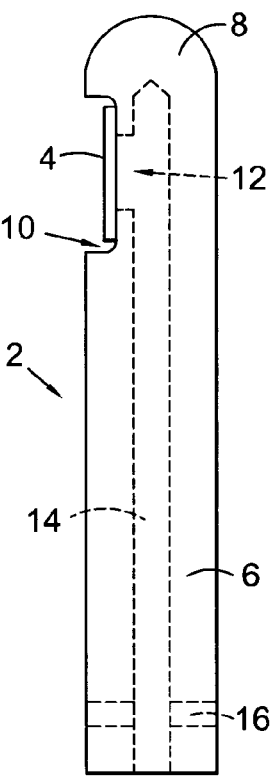
Fig.1　　Fig.2　　Fig.3
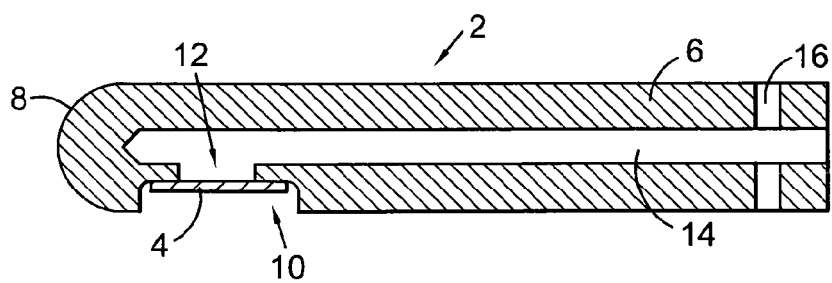
Fig.4
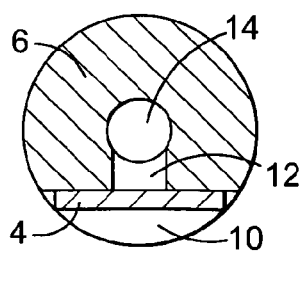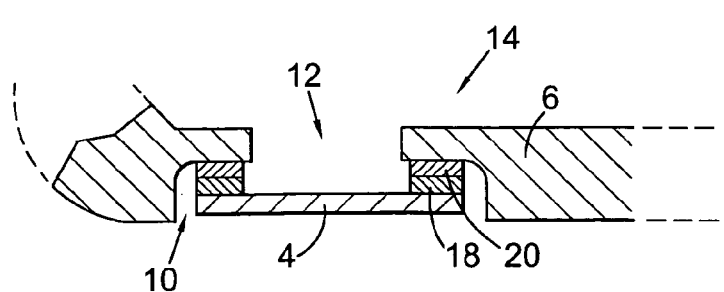
Fig.5　　Fig.6

DIAMOND WINDOW COMPONENT FOR A LASER TOOL

FIELD OF INVENTION

The present invention relates to a diamond window component for a laser tool. Certain embodiments relate to a laser medical probe.

BACKGROUND OF INVENTION

The use of diamond as a window material in a laser tool is known. Diamond is useful as a window material as it has low absorption for infrared wavelengths in order to transmit a high power laser beam.

One such use is in a medical laser probe comprising an optical fibre for transmitting a laser beam to a point within the body where a surgical procedure is to be performed. For example, JP 9028715, JP 5095962, U.S. Pat. No. 4,170,997 and U.S. Pat. No. 6,104,853 disclose the use of diamond as a window material disposed in the end of a medical laser probe. Medical laser probes can be used to perform surgical procedures including, for example, cutting and/or ablating tissue. Using a laser rather than a standard cutting tool can be advantageous in that the tissue is cauterized reducing blood loss and increasing healing rate. For such a use, diamond has the additional advantage over other possible window materials in that it is mechanically strong, inert, and biocompatible.

Many laser tools must be relatively small in size for their intended application. For example, in the medical device field, one use of laser tools is for treatment of the prostate, particularly for treatment of Benign Prostatic Hypertrophy (BPH). BPH is a common condition which involves the prostate becoming enlarged with aging causing the prostatic urethra to close off To treat this condition, a laterally firing laser tool can be placed within the prostatic urethra to direct a laser beam against the wall of the prostate to remove obstructing prostate tissue. Examples of such tools are described in U.S. Pat. No. 5,322,507, US 2009/0287197, and US 2009/0287199. Each of these documents discloses a laser tool comprising an optical fibre for transmitting a laser beam and an end component in the form of a tubular body defining an internal channel and an aperture through which the laser beam can pass out of the tubular body to the site requiring treatment. None of these documents disclose a diamond window.

The present inventors have envisaged using a diamond window in devices similar in structure to those described in U.S. Pat. No. 5,322,507, US 2009/0287197, and US 2009/0287199. However, it has been found that the diamond window has a tendency to de-bond from the device. A similar problem can also occur in devices of the type described in JP 9028715, JP 5095962, U.S. Pat. No. 4,170,997 and U.S. Pat. No. 6,014,853 where the diamond window is placed in the end of the tubular body rather than in a side thereof.

This may be particularly dangerous if de-bonding/delamination occurs while the medical device is being used as the diamond window is inherently very hard and can lacerate the surrounding tissue. More invasive surgery may then be required in order to remove the diamond window and repair any damage caused by the window.

It is an aim of certain embodiments of the present invention to solve the aforementioned problem. In particular, certain embodiments of the present invention seek to provide a laser tool which is stable, reliable, has improved lifetime, and can be made small in size.

SUMMARY OF INVENTION

The present inventors have traced the problem of diamond window de-bonding to a thermal mismatch between the diamond window and the tubular body to which it is bonded. It has been found that the small end tip of the laser tool becomes very hot during operation. Temperatures of approximately 200° C. have been observed. This heating effect is exacerbated by the small size of the end tip which requires relatively little energy to rapidly increase in temperature. The increase in temperature causes the diamond window and the tubular body to expand at different rates causing stress at the joint between the diamond window and the tubular body. This is because diamond has a much lower coefficient of thermal expansion compared with standard materials used to form the tubular body such as stainless steel. If the stress becomes too large, then the joint fails and the window de-bonds from the tubular body. Repeated heating and cooling in use can exacerbate this problem. Furthermore, autoclaving the apparatus in order to sterilize the apparatus between uses can also exacerbate this problem.

A similar problem can also occur during manufacture of the component if any thermal processing steps are utilized. For example, if the diamond window is welded or brazed to the tubular body, strain generated during cooling of the component due to a mismatch in thermal expansion coefficient can cause the diamond window to de-bond.

One way to alleviate some of the aforementioned problems is to provide an efficient cooling system to prevent the end tip from heating too rapidly or becoming too hot. However, incorporating an efficient cooling system can increase the size and complexity of the device which is not desirable.

An alternative possibility is to provide a flexible joint between the diamond window and the tubular body. However, flexible joints such as polymer adhesives are susceptible to melting and burning during use and/or are not suitable for autoclaving.

An alternative possibility for solving the aforementioned problem it to manufacture the tubular body from a material which has a coefficient of thermal expansion closer to that of diamond than standard medical grade stainless steel. In this regard, stainless steel has a coefficient of linear thermal expansion $\alpha$ of approximately $17 \times 10^{-6}$ $K^{-1}$ at 20° C. (this value varies depending on the particular formulation of stainless steel). Diamond has a coefficient of linear thermal expansion $\alpha$ of $1.1 \times 10^{-6}$ $K^{-1}$ at 20° C. As such, manufacturing the tubular body from a material such as titanium (which has a coefficient of linear thermal expansion $\alpha$ of $8.6 \times 10^{-6}$ $K^{-1}$ at 20° C.) would be expected to alleviate the problem of diamond window delamination. In practice however, it was found that this did not solve the problem.

The present inventors traced the problem with the titanium tubular body arrangement to the relatively poor thermal conductivity of titanium. Titanium has a thermal conductivity of about 21 $Wm^{-1}$ $K^{-1}$ at 20° C. Heat build up at the tip of the laser tool around the diamond window is exacerbated if the heat cannot be conducted away from the diamond window. As such, even though the thermal expansion coefficient of titanium and diamond are better matched, a large and rapid increase in temperature during use due to the poor thermal conductivity of titanium offsets this benefit.

One possible way to solve the aforementioned problem is to use a material for the tubular body which has a very high thermal conductivity such as silver (which has a thermal conductivity of 429 $Wm^{-1}$ $K^{-1}$ at 20° C.) or copper (which has a thermal conductivity of 393 $Wm^{-1}$ $K^{-1}$ at 20° C.). However, it was found that even though local heat build-up around the diamond window can be reduced using such materials, the thermal expansion coefficients of these materials are too large ($19.5 \times 10^{-6}$ K$^{-1}$ at 20° C. for silver and $16.6 \times 10^{-6}$ K$^{-1}$ at 20° C. for copper). As such, a lower and slower increase in temperature is still sufficient to generate enough stress for the diamond window to delaminate from the tubular body.

In light of the above, the present inventors have found that in order to solve the problem of diamond window delamination the tubular body to which it is bonded must be made of a material having a relatively low thermal expansion coefficient and a relatively high thermal conductivity.

As such, a first aspect of the present invention provides a component for a laser tool, the component comprising:
- a tubular body defining an internal channel and an aperture; and
- a window disposed across the aperture and bonded to the tubular body around the aperture,
- wherein the window is diamond, and
- wherein the tubular body comprises a material having a coefficient of linear thermal expansion $\alpha$ of $14 \times 10^{-6}$ K$^{-1}$ or less at 20° C. and a thermal conductivity of 60 Wm$^{-1}$ K$^{-1}$ or more at 20° C.

According to a second aspect of the present invention the component is attached to the end of an optical fibre for transmitting a laser beam. Such a tool may be incorporated into a catheter for medical applications such as laser treatment of the prostate.

The coefficient of linear thermal expansion $\alpha$ is advantageously $12 \times 10^{-6}$ K$^{-1}$ or less, $10 \times 10^{-6}$ K$^{-1}$ or less, $8 \times 10^{-6}$ K$^{-1}$ or less, $6 \times 10^{-6}$ K$^{-1}$ or less, or $4 \times 10^{-6}$ K$^{-1}$ or less.

The thermal conductivity is advantageously 60 Wm$^{-1}$ K$^{-1}$ or more, 80 Wm$^{-1}$ K$^{-1}$ or more, 100 Wm$^{-1}$ K$^{-1}$ or more, 120 Wm$^{-1}$ K$^{-1}$ or more, or 140 Wm$^{-1}$ K$^{-1}$ or more.

The tubular body may be formed of at least 50% of the low thermal expansion coefficient/high thermal conductivity material. More preferably, the tubular body is formed of at least 70% of said material, at least 80% of said material, at least 90% of said material, or at least 95% of said material. The material may be a metal, an alloy, a ceramic, or a composite material. Examples of such materials include one or more of molybdenum, chromium, tungsten, nickel, rhodium, ruthenium, silicon carbide (SiC), tungsten carbide (WC), aluminium nitride (AlN), molybdenum alloys such as titanium zirconium molybdenium (TZM), and tungsten alloys such as tungsten nickel iron (WNiFe) and tungsten nickel copper (WNiCu). Another possibility is to manufacture the tubular body from a diamond material such as polycrystalline chemical vapour deposited (CVD) diamond.

Molybdenum has been found to be particularly useful as it can readily be manufactured into a tubular body, has a low thermal expansion coefficient of $5 \times 10^{-6}$ K$^{-1}$, and has a relatively high thermal conductivity of 144 Wm$^{-1}$ K$^{-1}$. For medical applications, the tubular body may be coated with a biocompatible material. A suitable biocompatible material is gold.

The diamond may be single crystal or a polycrystalline diamond material. Furthermore, the diamond may be CVD diamond material, high pressure high temperature (HPHT) diamond material or natural diamond. The diamond material should preferably be of an optical grade and may have an absorption coefficient 13 equal to or less than 0.1 cm$^{-1}$, more preferably less than or equal to 0.05 cm$^{-1}$, at an operating wavelength of the laser tool. An exemplary operating wavelength is 532 nm. However, due to diamond material's low absorption across the infrared and visible region of the spectrum, other operating wavelengths may be utilized. For example, a $CO_2$ laser at 10.6 µm may be utilized.

In addition to the problem of the diamond window debonding from the tubular body, the present inventors have identified another problem associated with undue heating of the diamond window in a laser tool. As stated in U.S. Pat. No. 4,170,997, diamond has a high refractive index. As such, U.S. Pat. No. 4,170,997 teaches that it is advantageous to apply an antireflective coating to the diamond window to maximize light transmission. This may be applied on one or both sides of the diamond window. Indeed, it is well known to use such an antireflective coating when using diamond as a window material for other optical application. However, when used in small devices such as medical probes, the present inventors have found that heating during operation leads to delamination of the antireflective coating. Delamination of the antireflective coating can lead to the formation of hot-spots in the window material and possible fracture of the window. Accordingly, for small devices it is advantageous to use a diamond window without an antireflective coating.

The diamond window is advantageously provided with a metallization coating on an internal surface in an area around the aperture. Such a coating aids bonding between the diamond window and the tubular body. A preferred metallization coating comprises a layer of a carbide forming material such as titanium, an inert barrier layer such as platinum, and a metal layer such as gold for soldering or brazing to the tubular body gold. The titanium provides a good bond with the diamond forming titanium carbide at an interface with the diamond. The gold provides a good bond to the tubular body. The platinum functions as an inert shield between the gold and titanium.

A braze joint can be provided between the metallization coating and the tubular body for bonding the diamond window to the tubular body. The braze joint may comprise gold or alternatively may comprise copper and silver. A copper and silver braze has been found to be particularly useful as it provides a very good thermal contact between the diamond window and the tubular body.

The tubular body may be selected to have a variety of possible shapes according to its intended use. For many applications a circular or oval cross-sectional shape will be suitable. As previously described, the present invention is particularly useful for small components. Accordingly, the largest external diameter of the tubular body may be 10 mm or less, 7 mm or less, 5 mm or less, 3.5 mm or less, 3.0 mm or less, or 2.6 mm or less. The term "largest external diameter" is simply the diameter when the tubular body has a circular cross section. When the tubular body has a non-circular cross-section, such as an oval cross-section, then the largest external diameter refers to the largest distance across the cross-section in a direction perpendicular to a longitudinal axis of the tubular body. It may also be noted that in the context of the present invention the tubular body has a length greater than its external diameter as is conventionally the case for a tubular body.

The tubular body may have a wall thickness of 0.5 mm to 2.5 mm, 0.5 mm to 2.0 mm, 0.5 mm to 1.5 mm, 0.7 mm to 1.2 mm, or 0.8 mm to 1.0 mm. Furthermore, the internal diameter of the tubular body may be 0.2 mm to 8 mm, 0.3 mm to 6 mm, 0.35 mm to 4 mm, 0.4 mm to 2.0 mm, 0.4 mm to 1.0 mm, or 0.5 mm to 0.8 mm. Diamond window de-bonding has been found to be problematic for such a small tubular body unless constructed of a material according to the present invention.

Similar comments apply having regard to the diamond window. That is, the present invention is particularly useful when applied to a small diamond window which is more susceptible to heating. Accordingly, the diamond window may have a thickness in the range 0.1 mm to 0.5 mm, 0.1 mm to 0.3 mm, 0.1 mm to 0.2 mm, or 0.1 mm to 0.2 mm. Furthermore, the diamond window may have a longest dimension in the range 1.0 mm to 10.0 mm, 1.0 mm to 8.0 mm, 1.5 mm to 5.0 mm, or 2.5 mm to 3.5 mm. Further still, the diamond window may have a width in the range 1.0 mm to 5.0 mm, 1.0 mm to 3 mm, or 1.5 mm to 2.5 mm.

The aperture of the tubular body may be disposed in an end or in a side wall of the tubular body. A side wall aperture is useful for applications which require a lateral-firing laser device such as that used to treat Benign Prostatic Hypertrophy. In such a lateral-firing device, the tubular body may have a closed end. A smooth end cap may be provided for medical applications to aid insertion of the device into the body. The device may have an internal reflector for deflecting the laser light in a lateral direction. Alternatively, a lateral-firing optical fibre may be used.

The aperture is advantageously elongate having a longest dimension extending along a length of the tubular body. This will allow for slight variations in the longitudinal position of an optical fibre disposed within the tubular body. An elongate diamond window may be provided for covering such an elongate aperture. As such, slight variations in attachment of the component to an optical fibre are tolerated. For example, the aperture may have a length in the range 1.0 mm to 8.0 mm, 1.0 mm to 5.0 mm, or 1.0 mm to 3 mm. Furthermore, the aperture may have a width in the range 0.5 mm to 5.0 mm, 0.5 mm to 3.0 mm, or 0.5 mm to 2.0 mm.

The overlap between the diamond window and a side wall of the tubular body around the aperture may be 0.2 mm to 1.0 mm, 0.3 mm to 0.8 mm, 0.35 mm to 0.6 mm, or more preferably 0.4 mm to 0.5 mm. The relative size of the diamond window and the aperture is selected to achieve a reliable bond between the diamond window and the tubular body around the aperture and to provide an optimal thermal contact between the diamond window and the tubular body.

One further problem which the present inventors have identified is that the diamond window can have very sharp edges causing lacerations during medical applications. As such, it has been found to be advantageous to position the aperture in a recess in the side wall of the tubular body and locate the diamond window in the recess across the aperture, the diamond window having an area less than an area of the recess and greater than an area of the aperture. This arrangement ensures that the diamond window extends across the entire aperture while being wholly located within the recess such that no sharp edges protrude out from the tubular body. In order to further negate the possibility of a diamond edge cutting into a patient, one or more edges of the diamond window can be chamfered such that they are flush to a wall of the tubular body.

The diamond window is preferably bonded to the tubular body around the aperture to form a seal all around the aperture. This will prevent fluid or other debris entering the tubular member and fouling the optical fibre.

BRIEF DESCRIPTION OF THE DRAWINGS

For a better understanding of the present invention and to show how the same may be carried into effect, embodiments of the present invention will now be described by way of example only with reference to the accompanying drawings, in which:

FIG. 1 shows a perspective view of a diamond window component for a laser tool according to an embodiment of the present invention;

FIG. 2 illustrates a front view of a diamond window component for a laser tool according to an embodiment of the present invention;

FIG. 3 illustrates a side view of a diamond window component for a laser tool according to an embodiment of the present invention;

FIG. 4 illustrates a side cross-sectional view of a diamond window component for a laser tool according to an embodiment of the present invention;

FIG. 5 illustrates an end cross-sectional view of a diamond window component for a laser tool according to an embodiment of the present invention; and FIG. 6 illustrates a portion of a diamond window component for a laser tool showing a bonding arrangement between a diamond window and a tubular body.

DETAILED DESCRIPTION OF CERTAIN EMBODIMENTS

FIGS. 1 to 6 show various views of a diamond window component for a laser tool such as a medical probe for treating Benign Prostatic Hypertrophy. The component comprises a tubular body 2 and a diamond window 4. The tubular body 4 comprises an elongate hollow tube 6 and an end cap 8. The diamond window 4 is disposed in a recess 10 in a side wall of the elongate hollow tube 6. An aperture 12 is disposed in the side wall of the elongate hollow tube 6 under the diamond window 4 which allows laser light to pass from an interior channel 14 in the elongate hollow tube 6 out through the diamond window 4.

An end of the tubular body 2 opposite the end cap 8 is configured for attachment to an end of an optical fibre to transmit laser light down the interior channel 14. In the illustrated embodiment, an optical fibre can be inserted into the interior channel 14 and secured with screws 16 as shown in FIGS. 3 and 4. The optical fibre may be of the side-firing type. Alternatively, if an end-firing optical fibre is utilized, an angled reflector (not shown) may be provided in the interior channel 14 opposite to the aperture 12 for directing laser light from an end of an optical fibre through the diamond window 4.

The diamond window 4 is bonded to the tubular body 2 in the recess 10 such that the diamond window 4 forms a seal around the aperture 12. A metallization coating 18 is provided on an interior surface of the diamond window to aid bonding. The metallization coating comprises titanium, platinum, and gold and forms a picture frame arrangement around the aperture 12. The metallization coating 18 is bonded to the tubular body 2 in the recess 10 via a braze or solder 20 of, for example, copper and silver.

The tubular body 2 has a length of 15 mm, a diameter of 2.5 mm, and a wall thickness of 0.9 mm. The diamond window 4 has a length of 3 mm, a width of 1.8 mm, and a thickness of 0.15 mm. The recess 12 has a length of 3.2 mm, a width of 2.0 mm, and a depth of 0.55 mm. The aperture 12 has a length of 2.0 mm, a width of 1.0 mm, and a depth of 0.4 mm. The interior channel 14 has a diameter of 0.6 mm.

In use, the component is attached to the end of an optical fibre to form a medical laser probe. The small size of the probe allows insertion into narrow passages such as the prostatic urethra. The high thermal conductivity of the diamond and molybdenum allows heat to be conducted away from the diamond window. The high thermal conductivity of the copper and silver braze also aids in providing a good thermal contact between the diamond window and the tubular body for conducting heat away from the diamond window in use.

The relatively small difference in thermal expansion coefficient between the diamond window and the molybdenum tubular body aids in reducing differences in thermal expansion in use. Stress at the joint between the tubular body and the diamond window is reduced when compared with prior art arrangements and failure of the bonding between the diamond window and the tubular body is prevented. The provision of a metallization coating of titanium, platinum, and gold also aids in preventing de-lamination of the diamond window from the tubular body in use.

The location of the diamond window in a recess in the side wall of the tubular body prevents edges of the diamond window from damaging tissue in use. Furthermore, the relative size of the diamond window and the aperture is selected to achieve a reliable bond between the diamond window and the tubular body around the aperture and to provide an optimal thermal contact between the diamond window and the tubular body.

Although the present invention has been developed as a medical probe, it is envisaged that the invention could be applied to laser probes in other technical fields. For example, a probe which uses a laser optical fibre and an end component as described herein could be used to cut or weld metal tubes on an interior side thereof. Accordingly, while this invention has been particularly shown and described with reference to preferred embodiments, it will be understood to those skilled in the art that various changes in form and detail may be made without departing from the scope of the invention as defined by the appendant claims.

The invention claimed is:

1. A component for a laser tool, the component comprising:
a tubular body defining an internal channel and an aperture; and
a window disposed across the aperture and bonded to the tubular body around the aperture,
wherein the window is diamond, and
wherein the tubular body comprises a material having a coefficient of linear thermal expansion $\alpha$ of $12\times10^{-6}$ $K^{-1}$ or less at 20° C. and a thermal conductivity of 80 $Wm^{-1}$ $K^{-1}$ or more at 20° C.

2. A component according to claim 1, wherein $\alpha$ is $10\times10^{-6}$ $K^{-1}$ or less.

3. A component according to claim 1, wherein the thermal conductivity is 100 $Wm^{-1}$ $K^{-1}$ or more.

4. A component according to claim 1, wherein the tubular body is formed of at least 50% of said material.

5. A component according to claim 1, wherein said material is a metal, an alloy, a ceramic, or a composite material.

6. A component according to claim 1, wherein said material comprises one or more of molybdenum, chromium, tungsten, rhodium, ruthenium, diamond, silicon carbide (SiC), tungsten carbide (WC), aluminium nitride (AlN), titanium zirconium molybdenium (TZM), tungsten nickel iron (WNiFe), and tungsten nickel copper (WNiCu).

7. A component according to claim 1, wherein the tubular body is formed of molybdenum.

8. A component according to claim 1, wherein the tubular body is coated with a biocompatible material.

9. A component according to claim 1, wherein the diamond window is free of antireflective coating in an area across the aperture.

10. A component according to claim 1, wherein the diamond window is provided with a metallization coating forming at least a portion of a bond between the diamond window and the tubular body.

11. A component according to claim 10, wherein the metallization coating comprises a layer of carbide forming material bonded to the diamond window, an inert barrier layer, and a metal layer soldered or brazed to the tubular body.

12. A component according to claim 11, wherein the carbide forming material is titanium, the inert barrier layer is platinum, and the metal layer is gold.

13. A component according to claim 10, wherein the bond further comprises a braze joint between the metallization coating and the tubular body.

14. A component according to claim 13, wherein the braze joint comprises gold.

15. A component according to claim 1, wherein the aperture is in a side wall of the tubular body.

16. A component according to claim 1, wherein $\alpha$ is $8\times10^{-6}$ $K^{-1}$ or less.

17. A component according to claim 1, wherein $\alpha$ is $6\times10^{-6}$ $K^{-1}$ or less.

18. A component according to claim 1, wherein $\alpha$ is $4\times10^{-6}$ $K^{-1}$ or less.

19. A component according to claim 1, wherein the thermal conductivity is 120 $Wm^{-1}$ $K^{-1}$ or more.

20. A component according to claim 1, wherein the thermal conductivity is 140 $Wm^{-1}$ $K^{-1}$ or more.

21. A component according to claim 1, wherein the tubular body is formed of at least 70% of said material.

22. A component according to claim 1, wherein the tubular body is formed of at least 80% of said material.

23. A component according to claim 1, wherein the tubular body is formed of at least 90% of said material.

24. A component according to claim 1, wherein the tubular body is formed of at least 95% of said material.

25. A component according to claim 13, wherein the braze joint comprises copper and silver.

* * * * *